US010238244B2

(12) United States Patent
Gordon et al.

(10) Patent No.: US 10,238,244 B2
(45) Date of Patent: Mar. 26, 2019

(54) PERSONAL CARE CLEANING ARTICLE

(71) Applicant: Kimberly-Clark Worldwide, Inc, Neenah, WI (US)

(72) Inventors: Alice Susan Gordon, Roswell, GA (US); Jonathan Adam Dien, Chicago, IL (US); Nadeem Haidary, San Francisco, CA (US); Cynthia Watts Henderson, Neenah, WI (US); Jennifer L Schiffman, Chicago, IL (US); Kimberly J Tempas, Neenah, WI (US)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 350 days.

(21) Appl. No.: 14/992,688

(22) Filed: Jan. 11, 2016

(65) Prior Publication Data

US 2016/0120374 A1 May 5, 2016

Related U.S. Application Data

(62) Division of application No. 14/045,448, filed on Oct. 3, 2013, now Pat. No. 9,259,075.
(Continued)

(51) Int. Cl.
*A47K 7/02* (2006.01)
*A47K 7/03* (2006.01)
(Continued)

(52) U.S. Cl.
CPC ................ *A47K 7/02* (2013.01); *A45D 34/04* (2013.01); *A45D 44/22* (2013.01); *A47K 7/03* (2013.01);
(Continued)

(58) Field of Classification Search
CPC .... A45D 2200/1018; A45D 2200/1036; A45D 2200/1054; A45D 2200/1063;
(Continued)

(56) References Cited

U.S. PATENT DOCUMENTS

D55,474 S 6/1920 Koon
2,665,528 A * 1/1954 Sternfield .............. B24D 11/00 15/104.93
(Continued)

FOREIGN PATENT DOCUMENTS

EP 0 068 830 A1 1/1983
EP 0 945 251 A1 9/1999
(Continued)

OTHER PUBLICATIONS

Machine translation of JP2000-247893A dated Sep. 2000 (Year: 2000).*

*Primary Examiner* — Douglas Lee

(57) ABSTRACT

The present invention provides personal cleaning articles useful for cleaning and/or exfoliating the skin. These articles provide multiple distinct patterns of relatively smooth and coarse elements to provide a user the ability to readily achieve the desired degree of cleansing and/or exfoliation. Further, the article provides a relatively smooth apertured outer layer and a relatively coarse underlying layer whereby a user can, with the application of varied amounts of pressure, more readily achieve and control a wider range of mechanical cleaning and/or exfoliating action against the skin. In certain aspects, the article may also be impregnated with one or more topical skin cleaning and/or exfoliating compounds.

20 Claims, 5 Drawing Sheets

Related U.S. Application Data

(60) Provisional application No. 61/710,300, filed on Oct. 5, 2012.

(51) Int. Cl.

| | |
|---|---|
| ***A47L 13/16*** | (2006.01) |
| ***A47L 13/17*** | (2006.01) |
| ***B08B 1/00*** | (2006.01) |
| ***A45D 44/22*** | (2006.01) |
| ***A45D 34/04*** | (2006.01) |

(52) U.S. Cl.

CPC ...... *B08B 1/006* (2013.01); *A45D 2200/1018* (2013.01); *A45D 2200/1036* (2013.01); *A45D 2200/1054* (2013.01); *A45D 2200/1063* (2013.01); *A47L 13/16* (2013.01); *A47L 13/17* (2013.01); *B08B 1/003* (2013.01)

(58) Field of Classification Search

CPC .......... A45D 34/04; A45D 44/22; A47K 7/02; A47K 7/03; A47L 13/16; A47L 13/17; B08B 1/006; B08B 1/003

See application file for complete search history.

(56) References Cited

U.S. PATENT DOCUMENTS

| | | | | | |
|---|---|---|---|---|---|
| 3,374,882 | A | | 3/1968 | Amaliksen | |
| 4,769,022 | A | | 9/1988 | Chang et al. | |
| 4,832,942 | A | | 5/1989 | Crace | |
| 5,258,220 | A | * | 11/1993 | Joseph | A47L 13/17 442/346 |
| 5,594,970 | A | | 1/1997 | Benge | |
| D381,461 | S | * | 7/1997 | Gerhartl | D28/8 |
| 5,738,212 | A | | 4/1998 | Pollard et al. | |
| 5,744,149 | A | | 4/1998 | Girardot | |
| 5,904,151 | A | | 5/1999 | Gueret | |
| 6,006,761 | A | | 12/1999 | Meledandri | |
| 6,077,581 | A | * | 6/2000 | Kuramochi | B24B 37/11 428/323 |
| 6,132,841 | A | | 10/2000 | Guthrie et al. | |
| 6,226,811 | B1 | | 5/2001 | Fagan | |
| 6,325,565 | B1 | | 12/2001 | Girardot et al. | |
| 6,491,928 | B1 | | 12/2002 | Smith, III | |
| 6,513,184 | B1 | | 2/2003 | Brown et al. | |
| D476,080 | S | | 6/2003 | Hantke et al. | |
| 6,669,387 | B2 | | 12/2003 | Gruenbacher et al. | |
| D490,566 | S | | 5/2004 | Bergquist et al. | |
| D492,816 | S | | 7/2004 | Bergquist et al. | |
| 6,783,294 | B2 | | 8/2004 | Duden et al. | |
| 6,834,619 | B1 | | 12/2004 | Rampersad | |
| 7,020,929 | B1 | * | 4/2006 | Cantonis | A47L 13/16 15/209.1 |
| 7,115,535 | B1 | | 10/2006 | Smith, III et al. | |
| D545,969 | S | | 7/2007 | Eknoian et al. | |
| D545,970 | S | | 7/2007 | Eknoian et al. | |
| 7,488,697 | B2 | | 2/2009 | Louis Dit Picard et al. | |
| 7,612,031 | B2 | | 11/2009 | Lang et al. | |
| 8,017,145 | B2 | | 9/2011 | Hart et al. | |
| 2002/0087168 | A1 | | 7/2002 | Winitsky | |
| 2002/0107528 | A1 | | 8/2002 | Vayrette | |
| 2003/0031703 | A1 | | 2/2003 | McMeekin et al. | |
| 2003/0104036 | A1 | | 6/2003 | Gregoire | |
| 2004/0111817 | A1 | | 6/2004 | Chen et al. | |
| 2004/0253297 | A1 | | 12/2004 | Hedges et al. | |
| 2005/0129897 | A1 | | 6/2005 | Zhou et al. | |
| 2005/0136099 | A1 | * | 6/2005 | Hart | A61K 8/0208 424/443 |
| 2005/0159063 | A1 | * | 7/2005 | Hill | A47L 13/16 442/327 |
| 2006/0010630 | A1 | | 1/2006 | Tse | |
| 2006/0135026 | A1 | | 6/2006 | Arendt et al. | |
| 2007/0082032 | A1 | | 4/2007 | Gregoire et al. | |
| 2007/0098768 | A1 | | 5/2007 | Close et al. | |
| 2007/0256261 | A1 | | 11/2007 | Benitez, Jr. et al. | |
| 2007/0269469 | A1 | | 11/2007 | Hall-Maxwell | |
| 2009/0019656 | A1 | * | 1/2009 | Mitchell | A47K 7/02 15/208 |
| 2009/0068409 | A1 | | 3/2009 | Bret et al. | |
| 2010/0229320 | A1 | | 9/2010 | Lee | |
| 2013/0198989 | A1 | | 8/2013 | Jemsby et al. | |

FOREIGN PATENT DOCUMENTS

| | | | | |
|---|---|---|---|---|
| EP | 1 136 024 | A2 | | 9/2001 |
| EP | 1 350 456 | A1 | | 10/2003 |
| EP | 1 541 079 | A1 | | 6/2005 |
| EP | 1 764 077 | A2 | | 3/2007 |
| EP | 1 994 853 | A1 | | 11/2008 |
| EP | 2 468 235 | A1 | | 6/2012 |
| FR | 2 860 525 | B1 | | 2/2006 |
| GB | 1 417 293 | A | | 12/1975 |
| JP | 2000247893 | A | * | 9/2000 |
| JP | 2004-249061 | A | | 9/2004 |
| JP | 1290631 | S | | 1/2007 |
| JP | 1290633 | S | | 1/2007 |
| WO | WO 1999/021532 | A1 | | 5/1999 |
| WO | WO DM/064070 | | | 6/2003 |
| WO | WO 2012/132981 | A1 | | 10/2012 |

* cited by examiner

PERSONAL CARE CLEANING ARTICLE

RELATED APPLICATIONS

The present application is a divisional application and claims priority to U.S. patent application Ser. No. 14/045,448, filed on Oct. 3, 2013, and claims priority to U.S. provisional Patent Application No. 61/710,300 filed on Oct. 5, 2012, the entire contents of which are incorporated herein by reference.

FIELD OF THE INVENTION

The present invention relates to disposable cleaning articles useful for personal care applications such as skin cleaning and/or exfoliating. Consumers use the articles by wetting the articles and rubbing the articles against the body in order to obtain the desired cleaning, exfoliating and/or other beneficial treatment.

BACKGROUND

Various disposable or single-use personal care cleaning articles are known and available today. Such articles are commonly used to remove dirt, oils, make-up as well as other undesirable matter from the body. In addition to basic personal cleaning, articles are also available that provide a deeper cleaning of the skin (epidermis) and that more effectively remove dead skin cells (corneocytes) from the outer most layer of the skin (stratus corneum). This process of removing dead skin cells from the outer most layer of the skin is commonly referred to as exfoliating. One of the perceived benefits from exfoliating is that a user's exfoliated skin appears fresh and healthy after the outer dull looking layer of dead skin cells are removed. The skin is constantly replenishing itself and producing new layers of dead skin cells. Thus, exfoliation is a process frequently utilized by many users. Exfoliating has long been accomplished through the use of relatively abrasive material such as a loofa or pumice. However, such highly abrasive materials can cause irritation and discomfort for many users. In addition, such traditional articles often fail to adequately remove residue from the skin formed or liberated in the process.

Less abrasive cleansing articles are known such as through the use of polymeric netting or sheet materials having polymer nodules thereon; by way of example such materials are described in U.S. Pat. No. 5,594,970 to Benge and US2003/0031703 McMeekin et al. In addition, there also exist two-sided cleanings pads that enable the user to choose between relatively rough and smooth sides. Examples of such two-sided pads are described in U.S. Pat. No. 5,744,149 Girardot, U.S. Pat. No. 7,488,697 Louis Dit Picard et al., and US2007/0098768 Close et al. However, the desired level of roughness or mechanical scrubbing action an article provides can vary significantly from user to user. In addition, the desired level of cleaning and/or exfoliating may frequently vary according to the user's experience on a given day; e.g. intense exercise, exposure to high levels of dirt or grime, sun exposure, the use of certain types of make-up and so forth. Furthermore, many individual users have what are perceived to be localized problem areas and therefore desire differing levels of roughness or mechanical scrubbing action for different regions of their face or body. Thus, existing pads fail to provide the wide range of variation and control desired by many users.

Therefore, there exists a need for a single-use or limited-use cleaning article that provides the user with the ability to easily obtain numerous different levels of roughness and/or mechanical scrubbing action. Further, there exists a need for a cleaning article that both effectively dislodges foreign or unwanted matter and that also effectively removes the same from the user's skin. Still further, there exists a need for such a pad with improved handleability in order to enable the user to fully utilize the pad and more easily achieve the desired treatment.

SUMMARY OF THE INVENTION

The present invention addresses the problems and/or shortcomings experienced with the cleaning pad designs of the prior art by providing a personal care cleaning article having a first side including first and second regions and wherein the first and second regions of the first side each have a pattern of interposed relatively smooth portions and recessed relatively rough portions and further wherein the ratio of the surface area of the rough portions of the first region to the surface area of the rough portions of the second region is not less than 1.15:1. In a further aspect, the rough portions comprise between about 5-65% of the total surface area of the first side of the article. In a further aspect, the first and second regions may each comprise between about 25% and about 50% of the first side of the article.

In still a further aspect of the invention, the patterns of rough portions within the first and second regions may be varied in one or more respects in order to provide regions with distinctly different hand-feel and/or mechanical cleaning action. For example the patterns may vary such that (i) the rough portions of the first region may have a larger average size, by area, than the average size of the rough portions in the second region; (ii) the rough portions of the first region include a greater number of rough portions than that contained within the second region; and/or (iii) wherein the average edge-to-edge distance between adjacent rough portions is smaller in the first region relative to that in second region. In still a further aspect, the dimensions of the individual rough portions are such that (i) they have a minimum diameter not less than 3 mm and maximum diameter not greater than 30 mm, and/or (ii) they present an area between 8 $mm^2$ and 700 $mm^2$. In still a further aspect the rougher and/or higher texture portions may comprise individual elements discretely located to one another. Further, in order to provide a more manageable tactile sensation and/or cleaning effect, the recessed rough portions may be located entirely below the outer surface of the surrounding smoother and/or lower texture portion.

In yet a further aspect of the invention, a personal cleansing article is provided comprising superposed first and second layers wherein the first layer includes a plurality of apertures each defining an area of not less than 8 $mm^2$ and further wherein the second layer has a rougher hand feel than the first layer and is physically contactable via the apertures in the first layer. In certain aspects, the apertures may comprise between about 5-65% of the first layer. In still further aspects of the invention, the individual apertures may (i) have minimum diameters that are at least 3 mm and maximum diameters not greater than 30 mm, and/or (ii) provide an open area or hole of between 8 $mm^2$ and 700 $mm^2$. In certain embodiments the first layer may include at least two clusters of apertures wherein the apertures forming the clusters vary in density, shape and/or size in order to provide regions with distinctly different hand-feel or cleaning action. Such individual regions may comprise between about 25% and about 50% of one side of the article.

The second layer of the cleaning article may comprise a material having protuberances thereon and that are exposed via the apertures. In certain aspects, the second layer may comprise a material having protuberances thereon and having an average diameter between about 75 microns and about 2000 microns. In still further aspects, the second layer may comprise polymeric fibrous materials including yarns and/or large fibers exposed on the surface that have an average diameter of between about 75 microns and about 2000 microns. In still a further aspect, the first layer may comprise a fibrous material having an average fiber diameter of less than about 50 microns.

In still further aspects of the invention, the cleaning article may further include a third layer joined to the first layer wherein the second layer is positioned between the first and third layers. Still further, the cleaning article may include a porous core member positioned between the second and third layers. In certain embodiments the porous core member may be resiliently deformable. Still further, an inner layer, such as the porous core member, may include a cleaning composition comprising a lathering surfactant.

In a further aspect, a personal care skin treatment article is provided comprising a fibrous web of polymeric fibers having opposed first and second sides and wherein the first side has interposed high texture portions and low texture portions. The high texture portions include a plurality of particles, nodules or tufted fibers located on the exposed outer surface of the first side that are entirely and/or substantially absent from the exposed outer surface of the low textured portions. Further, the first side has a first region having a first pattern of interposed high texture portions and low texture portions and a second region having a second pattern of interposed high texture portions and low texture portions wherein the first and second patterns vary in relation to one or more aspects selected from the group consisting of the number of the high texture portions, shape of the high texture portions, average size of the high texture portions and coverage area of high texture portions. In certain specific embodiments, regions and/or patterns may be selected such that (i) the first pattern comprises high texture portions that are at least 20% larger by area than the high texture portions of the second pattern, (ii) the surface area of the high texture portions in the first area is at least 15% greater than that in the second region, and/or (iii) the first region has a at least 15% more high texture portions per unit area than the second region.

In further aspects, the high texture portions may comprise between about 5-65% of the total surface area of the first region and second regions. In still further aspects, the high texture portions (i) are discretely positioned relative to one another, (ii) have a minimum diameter greater than 3 mm and a maximum diameter less than 30 mm, and/or (iii) have an area between 8 $mm^2$ and 700 $mm^2$. The first and second regions, and respective pattern of high and low texture portions, may be located proximate to the perimeter of the article and separated from one another such as, for example, along a radius and/or diameter line. In other embodiments, the first and second regions may be concentrically located relative to one another. In certain further aspects the first region and second regions, and their corresponding patterns, may be separated by a third region which, in certain embodiments, may lack any highly textured portions.

DESCRIPTION OF THE INVENTION

In reference to the Figures and throughout the specification and claims, discussion of the articles and/or individual components thereof is with the following understanding:

(i) the terms “comprising” or “including” are inclusive or open-ended and do not exclude additional unrecited elements, compositional components, or method steps. Accordingly, the terms “comprising” or “including” encompass the more restrictive terms “consisting essentially of” and “consisting of”;

(ii) the terms “inner” or “inwardly” generally refer to a position in or closer to the interior or core of the article and “outer” or “outwardly” generally refer to a position forming or closer to the exterior or outer surface of the article;

(iii) the terms “central” or “center” generally refers to a position at or about the center of the article when looking at a plan view as opposed to referring to the inner or interior portions of the article, stated differently the terms “center” or “central” portions shall mean portions distal to the periphery of the article;

(iv) the term “layer” includes materials substantially monolithic in composition and/or structure and also materials comprising multiple elements and/or sub-layers;

(v) the term “aperture” refers to an opening or hole that extends directly and completely through the thickness of a material or layer;

(vi) the terms “pore” or “porous” refers to open areas or interstitial spaces located within a material that do not individually extend through the thickness of the material, however such terms would not exclude the existence of tortuous pathways that extend through the thickness of the material via a series of adjacent and/or inter-connected pores.

Figure 1:
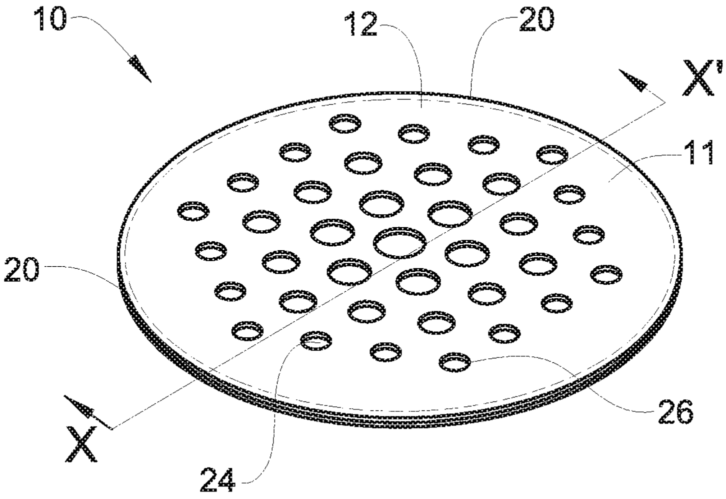
FIG. 1 is a top perspective view of a personal cleaning article of the present invention.
Figure 2:
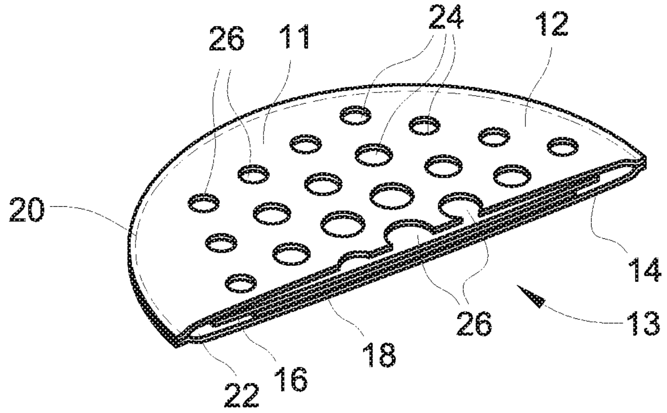
FIG. 2 is a cross-sectional view of the personal cleaning article of FIG. 1 taken at line X-X'.
Figure 3:
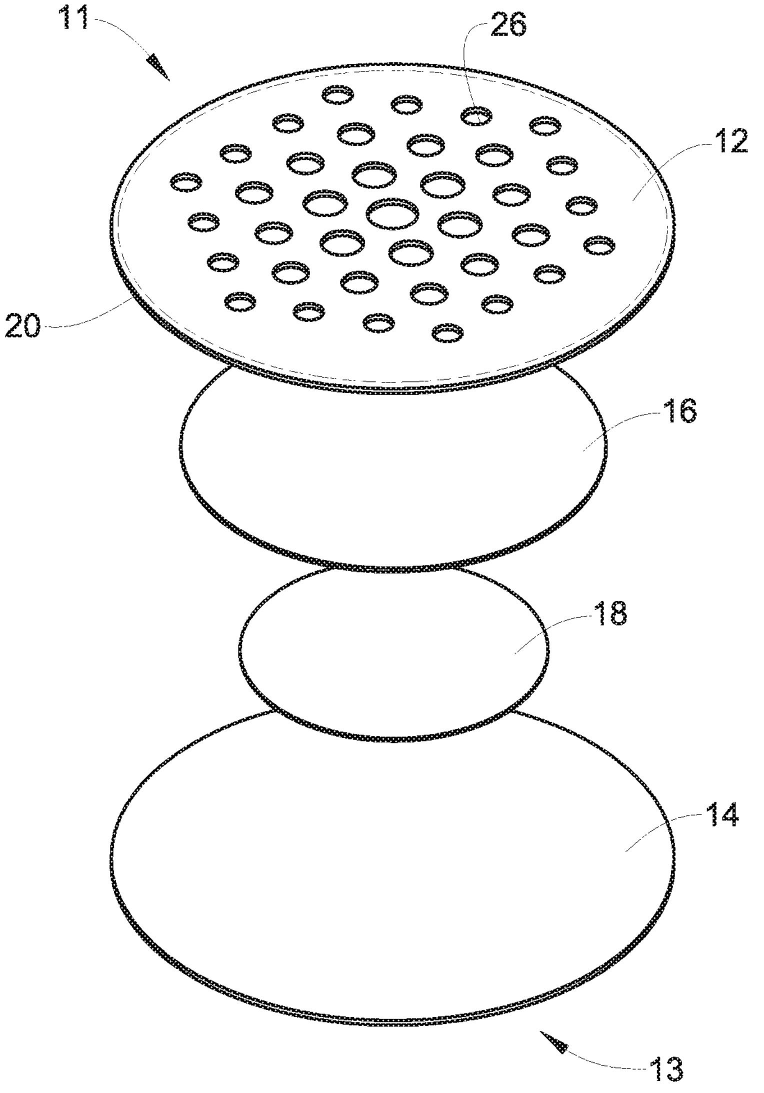
FIG. 3 is an exploded view of the personal cleaning article of FIG. 1.

In reference to the embodiments shown in FIGS. 1-3, a cleaning article 10 for personal use includes first and second outer layers 12, 14 respectively forming first and second sides 11, 13. The first and second outer layers 12, 14 may be joined at the edge or periphery 20 of article 10 to form an interior region or core 22. The exposed outer surface of the first side 11 includes a plurality of high texture areas such as may be formed by recessed scrubbing islands 24. Inwardly adjacent the first outer layer 12 is a scrubbing layer 16, portions of which are exposed by apertures 26 extending through the thickness of the first outer layer 12. In addition, the article 10 may further include one or more inner layers, such as a core member 18, to provide additional and/or enhanced functions. Thus, the article 10 can be used by a person to clean their skin, hair, nails and/or other individual body parts by wetting the article and then rubbing one or both of the first and second sides 11, 13 against the same to achieve the desired level and type of cleaning.

The size of the article 10 may be shaped and/or sized to provide sufficient surface area to enable a user to clean and/or treat the intended body part(s). By way of example, for many personal care applications it will be adequate for the article 10 to have a maximum diameter of between about 4-25 cm. In certain personal care applications, including use as a facial cleansing wipe and/or exfoliating article, the article 10 desirably has a maximum diameter of between about 5 cm and about 15 cm and in other embodiments may desirably have a maximum diameter of between about 5 cm and about 10 cm. The shape of the article 10 may vary as desired and may comprise rectilinear, curvilinear and irregular shapes. By way of example, the article may be circular, elliptical, oval, square, rectangular, multi-lobal and so forth. Desirably, the shape of the article 10 is such that it lacks any sharp corners. For example, as shown in reference to FIG. 5, a generally square shaped pad or article 10 is preferably provided with rounded corners.

The recessed scrubbing islands 24 may be selectively located across the outer surface of the first side 11 in order to provide the desired hand-feel and/or the desired degree of mechanical cleaning action. In this regard, the size and frequency of the recessed scrubbing islands 24 can be selected to impart higher or lower degrees of mechanical scrubbing action against the skin. The size of the recessed scrubbing islands 24 are sufficiently large such that, when a user presses and rubs the first side 11 of the article 10 against the skin, the scrubbing material directly contacts the skin to provide an effective mechanical cleaning action. The shape of the scrubbing islands 24 may vary including rectilinear, curvilinear and irregular shapes. By way of example, the scrubbing islands 24 may be circular, elliptical, triangular, square, rectangular, and so forth. Desirably, however, the scrubbing islands comprise shapes lacking any sharp corners; more specifically, it is desired that generally rectilinear shapes have rounded corners. In one aspect, the recessed scrubbing islands 24 are discretely located relative to one another.

The individual recessed scrubbing islands 24 are of a size and shape such that they have an area of at least 8 $mm^2$ exposed on the outer surface of the first side 11. The individual scrubbing islands desirably each comprise an area exposed on the outer surface of the first side between 8 $mm^2$ and about 700 $mm^2$, more desirably an area between about 12 $mm^2$ and 300 $mm^2$, and still more desirably an area between about 12 $mm^2$ and about 175 $mm^2$. In a further aspect, the scrubbing islands 24 desirably have a minimum diameter of at least about 3 mm and a maximum diameter of about 30 mm, and still more desirably may have a minimum diameter of about 4 mm and a maximum diameter of about 20 mm, and still further may have a minimum diameter of about 4 mm and a maximum diameter of about 15 mm. In still a further aspect, the scrubbing islands 24 comprise a sufficient amount of the total surface area of the outer surface of the first side 11 so as to effectively modify the hand-feel of the first outer layer as compared with the first outer layer lacking any recessed scrubbing islands. In this regard the recessed scrubbing islands desirably comprise between about 5%-65%, and still more desirably between about 5%-45% of the outer surface of the first side 11. In certain embodiments the recessed scrubbing layers may between about 10%-35% of the outer surface area of the first side 11.

Figure 5:
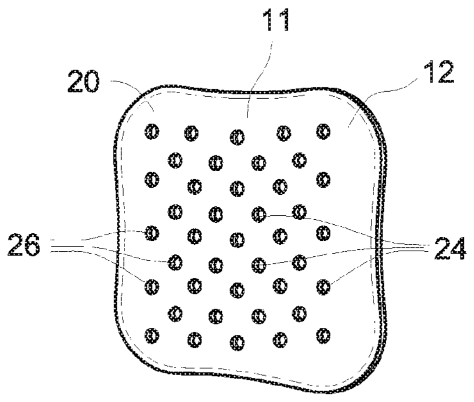
FIGS. 5-10 are top plan views of personal cleaning articles of the present invention having scrubbing islands located in various patterns.
Figure 6:
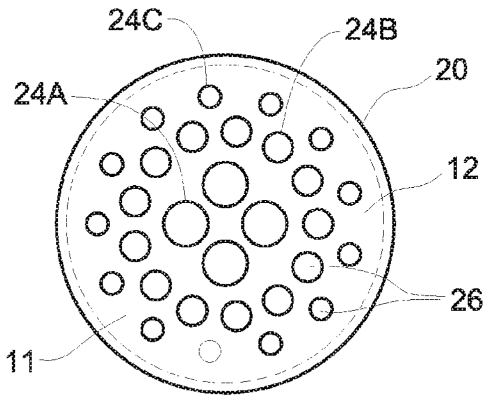
Figure 7:
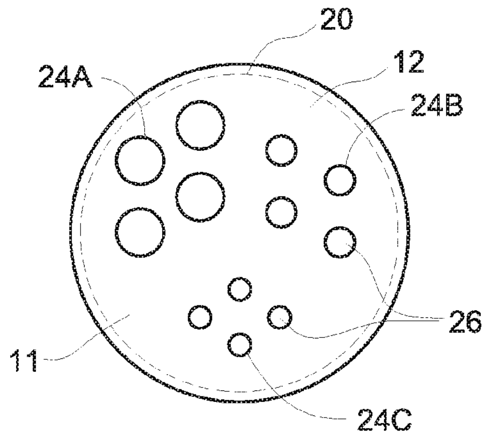

The scrubbing islands may be of uniform size and spacing across the first surface such as shown in reference to FIG. 5. However, the pattern of recessed scrubbing islands 24 is desirably varied regionally across the first side 11 to provide a single side having regions presenting distinctly different hand-feel and/or mechanical cleaning action. In one aspect, the first side 11 may be provided with recessed scrubbing islands having significantly different sizes, i.e. differing significantly in the amount of area exposed to the outer surface. As may be seen in reference to FIGS. 6 and 7, recessed scrubbing islands 24 are provided having different sized diameters and, in turn, different size areas exposed to the outer surface of the first side 11. The first side may be provided with a cluster of relatively larger diameter scrubbing islands 24A, a cluster of intermediate diameter scrubbing islands 24B and a cluster of relatively smaller diameter scrubbing islands 24C. In reference to FIG. 6, the clusters are concentrically located such that the diameter size of the scrubbing islands decreases towards the periphery of the pad; in other words the relatively larger diameter scrubbing islands 24A are located about the center of the article 10, the relatively smaller diameter scrubbing islands 24C are located proximate the periphery 20 and the intermediate size diameter scrubbing islands 24B are located there between. In reference to FIG. 7, the clusters are regionally located in generally "pie" shaped sections of the article and are separated by a radius line.

Figure 8:
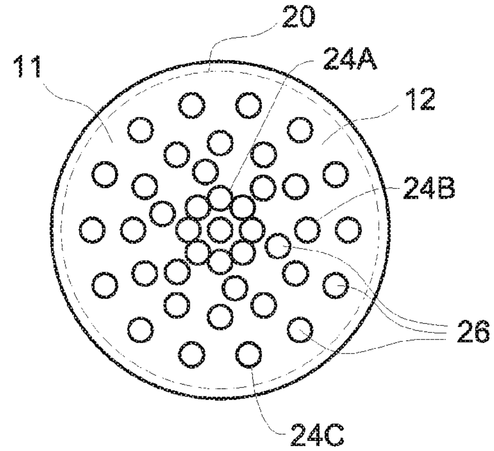
Figure 9:
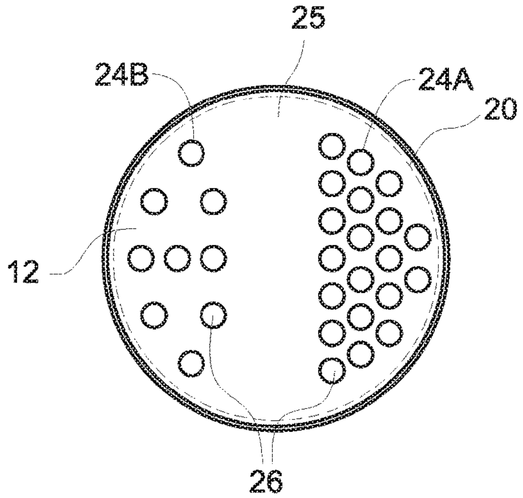
Figure 11:
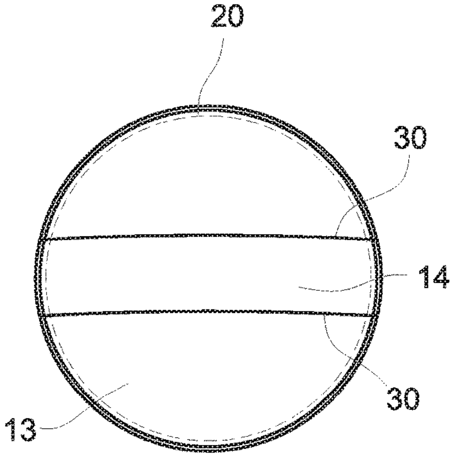
FIGS. 11 and 12 are back-side views of a personal cleaning article of the present invention displaying a pocket feature.

In a further aspect an article may be provided having sections presenting distinctly different hand-feel and/or cleaning action by providing clusters or regions with significantly different spacing as between adjacent scrubbing islands 24. By way of example and in reference to FIG. 8, the clusters are concentrically located such that the distance between adjacent scrubbing islands increases towards the periphery of the pad; the first side 11 includes a first cluster of the relatively closely spaced scrubbing islands 24A located about the center of the article 10, a second cluster of widely spaced scrubbing islands 24C located proximate the periphery 20 of the article 10 and a third cluster of intermediate spaced scrubbing islands 24B located there between. As a further example and in reference to FIG. 9, a first cluster of relatively closely spaced scrubbing islands 24A are provided in one section of the article and a second cluster of widely spaced scrubbing regions 24B are provided in an opposed section of the article. Located between the first and second clusters is an, 'island-free' section 25 lacking any apertures 26 or scrubbing islands 24; such a section may be employed as desired to aid the user's ability to quickly visually identify and use the distinct hand-feel sections.

Figure 10:
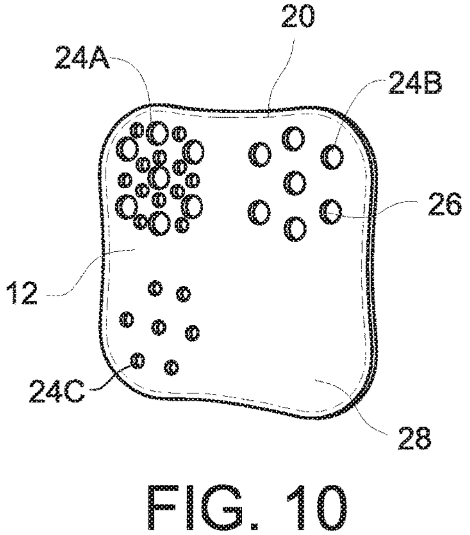
Figure 12:
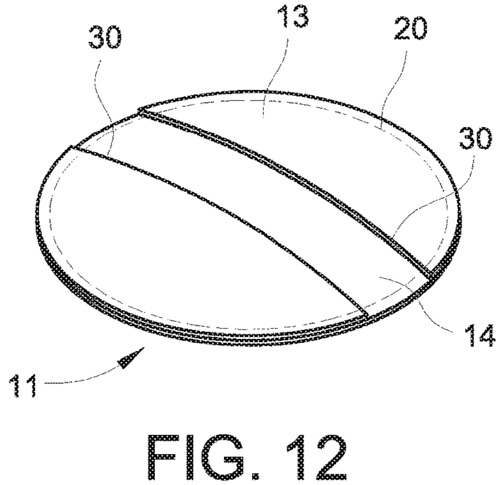

As still a further example, a single side having regions presenting distinctly different hand-feel and/or cleaning action may be provided by regionally varying the percentage of the surface area of the scrubbing islands exposed to the outer surface. In reference to FIG. 10, there is provided a first quadrant including a cluster of scrubbing islands 24A occupying a relatively higher percent of outer surface area, a second quadrant including a cluster of scrubbing islands 24B occupying an intermediate percent of the outer surface area and a third quadrant including a cluster of scrubbing islands 24C occupying a relatively low percent of the outer surface area. There is further provided an island-free section 28 or fourth quadrant lacking any scrubbing islands 24 whereby the fourth quadrant provides a relatively gentler hand-feel and soft wiping action than each of the three other quadrants.

High texture areas such as formed by scrubbing islands may be formed by one or more methods and comprise one or more structures. These areas are intended to provide a distinct hand or feel and, including, areas that provide a generally rough and/or abrasive texture. They may be formed integrally upon or within a single layer or formed as part of a multilayer structure. In one aspect and in reference to FIGS. 1-3, the scrubbing islands 24 may be formed by providing a first outer layer 12 having a plurality of apertures 26 which extend through the entire thickness of the first outer layer and that correspond in size and shape to the desired dimensions of the scrubbing islands 24. In this regard the apertures may have the same size and dimensions discussed herein above in reference to the recessed scrubbing islands 24. The apertures 26 directly expose the underlying scrubbing layer 16 to the outer surface of the first side 11 and provide a scrubbing surface that is located below the outer surface or plane of the first layer 12. The apertures may be integrally formed with the material comprising the first outer layer or, in the alternative, may be created within the material comprising the first outer layer post-formation. In one aspect, the apertures may be die-cut using a die having the desired number and pattern of cut-outs. In a further aspect, the apertures may be formed, particularly with thermoplastic fiber fabrics, using hot pins to form and stabilize apertures through the thickness of the fabric. By way of non-limiting example, comparable processes are described in U.S. Pat. No. 5,188,625 Van Iten et al. and U.S. Pat. No. 5,714,107 to Levy et al. In a further aspect, the apertures may be created integrally with the formation of the material such as by locally occluding web formation in defined locations so as to create apertures within the material at the time of formation. By way of non-limiting example, such processes are disclosed in U.S. Pat. No. 3,498,874 to Evans et al. and U.S. Pat. No. 5,575,874 to Griesbach et al.

The first outer layer 12 may be made from any suitable synthetic or natural material so as to provide a layer that is compliant and compressible to the touch. Desirably the first outer layer also has a soft, pleasing hand or feel and further is liquid permeable and sufficiently abrasion resistant to substantially avoid linting and/or pilling during use. Numerous materials are suitable for use in the first outer layer and include, but are not limited to, knit or woven fabrics, nonwoven fabrics, and porous open cell foams. Suitable polymers include, but are not limited to, polyolefins (e.g. polyethylene and polypropylene), polyesters (e.g. polyethylene terephthalate), polyamides (e.g. nylon), viscose, and mixtures thereof. Desirably, the first outer layer comprises a fibrous layer having a substantially uniform composition and is laid in such a manner so as to provide a substantially uniform outer surface. Non-limiting examples of suitable natural materials and derivatives thereof include woven and nonwoven materials made of fibers such as cotton, wood pulp, viscose or mixtures thereof. Exemplary nonwoven fabrics include, but are not limited to, spunlace (hydroentangled materials), spunbond, meltblown, and bonded-carded webs. Suitable materials include those described in U.S. Pat. No. 3,498,874 Evans et al., U.S. Pat. No. 3,849,241 to Butin et al., U.S. Pat. No. 4,340,563 to Appel et al., U.S. Pat. No. 4,443,513 to Meitner et al., U.S. Pat. No. 4,548,856 to Ali Kahn et al.; U.S. Pat. No. 4,853,281 to Abba et al.; U.S. Pat. No. 5,508,102 to Georger et al. U.S. Pat. No. 5,382,400 to Pike et al., U.S. Pat. No. 6,200,669 to Marmon et al., U.S. Pat. No. 6,224,977 to Kobylivker et al., and so forth.

The first outer layer has a basis weight and/or thickness that is sufficiently large so as to substantially occlude the coarseness and/or texture of underlying layers but not so high so as to prevent or impede direct unoccluded physical contact with the recessed scrubbing layer 16 through the aperture 26. In one aspect, the first outer layer desirably has a basis weight between about 50-175 g/M$^2$, and still more desirably between about 70-125 g/M$^2$. By way of a specific example, the first outer layer may comprise a thermally point bonded polypropylene meltblown fiber web having a basis weight of about 85 g/M$^2$. In certain embodiments, to assist with the provision of a comparatively smoother, lower texture and/or soft hand-feel, it may be desirable for the fibrous material to have an average fiber diameter less than about 50 microns.

Figure 4:
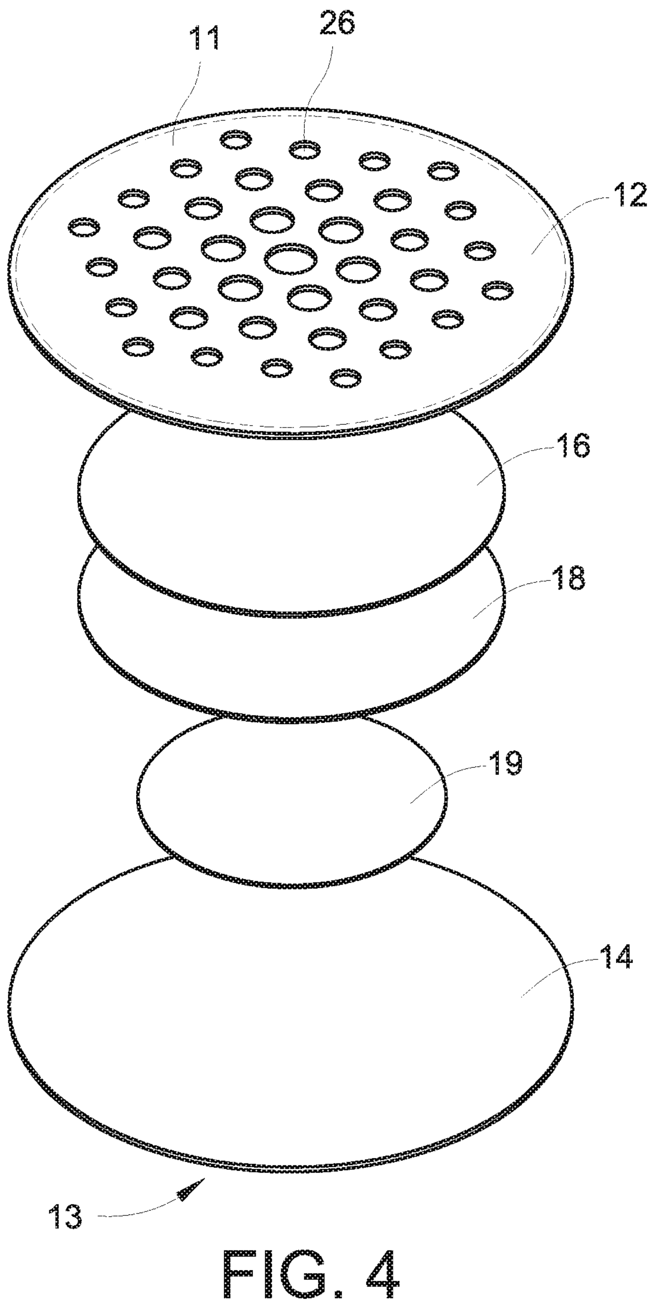
FIG. 4 is an exploded view of a personal cleaning article of the present invention.

The scrubbing layer 16 is located inwardly to and directly beneath the first outer layer 12. The scrubbing layer 16 can extend coterminously with the first outer layer 12, such as by extending to the outer edge of the article, or alternatively may extend only under a portion of the first outer layer 12. Desirably, and as shown in FIGS. 2-4, the scrubbing layer 16 is centrally located and extends under the majority of the apertures 26 within the first out layer, and still more desirably extends under all of the apertures 26 in the first outer layer 12. In one aspect, the scrubbing layer 16 may be colored so as to highlight for the user the presence of the scrubbing islands 24. By way of example, the first outer layer 12 may be white and the scrubbing layer may be purple whereby the scrubbing islands are readily visible to the user and improves the user's ability to identify and distinguish as between the different regions and scrubbing options on the first side. In still a further aspect, regions of scrubbing layer may itself be differently colored corresponding with the distinct regions and/or clusters of scrubbing islands exposed on the outer surface of the first side.

The scrubbing layer 16 is selected to have a distinctly different, e.g. rougher, hand-feel relative to that of the first outer layer 12. More specifically, the scrubbing layer 16 may be made from any suitable synthetic or natural material or blend thereof that is sufficiently coarser and/or highly textured (uneven) so as to provide a greater mechanical cleaning action against the skin. The messaging or mechanical cleaning action of the scrubbing layer 16 can be achieved by the use of materials including and/or having thereon the following: bound particles, formed and/or deposited polymeric nodules, fabrics or mesh having large diameter fibers or yarns, bonded fiber tufts, and so forth. By way of non-limiting example, various suitable materials for use in the scrubbing layer are described in U.S. Pat. No. 4,659,609 to Lamers et al., U.S. Pat. No. 4,769,022 to Chang et al., U.S. Pat. No. 5,067,400 Bezella et al., U.S. Pat. No. 5,594,970 to Benge; U.S. Pat. No. 5,786,065 Annis et al.; U.S. Pat. No. 5,874,160 to Keck, U.S. Pat. No. 6,713,156 Pauls et al.; US2003/0031703 McMeekin et al., and US2007/0098768 to Close et al., and so forth. In addition to the coarser hand-feel, the scrubbing layer 16 is desirably also liquid permeable and sufficiently durable to avoid any substantial linting, pilling or disintegration in use. Still further, the scrubbing layer is desirably compliant and easily manipulated and bent in use.

In certain embodiments, the scrubbing layer may comprise a fibrous material having protuberances or protrusions thereon such as nodules, fibrous projections or particles exposed on the outer surface thereof. The size and/or frequency of the protrusions may be varied to impart the desired hand-feel. The protrusions preferably have a diameter of at least about 100 microns and in further aspects such protrusions may have an average diameter between about 100-2000 microns and, more desirably, average diameters between about 200 microns and about 1000 microns.

In particular embodiments, nodules may be formed by depositing the same upon a preformed fabric. The nodules may be applied across the surface of the fabric or in one or more patterns as desired such as through the use of rotogravure or gravure printing (direct or indirect), flexographic printing, screen printing, stencil application and so forth. Suitable materials for forming nodules include, but are not limited to, polyolefins, ethylene vinyl acetate, thermoplastic elastomers, microcrystalline waxes, and natural or synthetic resins. Materials commonly utilized as hot-melt adhesives, and in particular oil-resistant hot-melt adhesives such as described in US2007/142801 to Campbell et al., may be used to form deposited polymeric nodule structures.

In certain embodiments, the scrubbing layer may be formed from a precursor web comprising a nonwoven substrate including low-temperature meltable binder fibers, which may be thermoplastic fibers. The binder fibers may be formed integrally with the web or may be added to an existing web through needling or entangling. The precursor web may be heated to cause the binder fibers to melt and form nodulated fiber remnants that impart an abrasive character to the resultant web material. In this regard it will be appreciated that in order to retain the web strength and shape, in addition to the binder fibers used to form nodulated remnants, the precursor web will also contain non-thermoplastic fibers (e.g. cotton and/or cellulosic fibers) and/or polymeric fibers having a higher melting point than the binder fibers. The precursor web may be wet laid, air laid, or made by other methods. As one example, the precursor web may comprise a bonded carded web having both nylon fibers and polypropylene fibers.

In additional embodiments, particles may be applied to the outer fibers of the layer of the scrubbing material and held in position on the fibers by use of an adhesive, binder or other material. The binder material and associated particulate material may be applied to the fabric layer either across substantially the entire outer surface or, in other embodiments, in one or more desired patterns. Methods of applying the binder and associated particulate material include spraying, dip and squeeze, foam treating, rotogravure or gravure printing (direct or indirect), flexographic printing, screen printing and so forth. Alternatively, fibers may be formed with the particulate material contained therein or, in the case of thermoplastic fibers, the fibrous web containing the particles may be heated so as to fixedly embed the particles in the fibers while in a semi-molten fibers. Particles suitable for use in adhering to the outer portion of the scrubbing material 16 can be derived from a wide variety of materials including those derived from inorganic, organic, natural, and synthetic sources. By way of non-limiting example, suitable particles include: seeds and powders thereof (e.g. Kiwi, cranberry, sunflower, raspberry, jojoba, etc.), botanical shell/husk powders (e.g. almond, coconut, pecan, walnut, wheat, etc.), oyster shell powder, jojoba esters, polymeric beads or powders (e.g. polybutylene, polyethylene, polyisobutylene, polymethylstyrene, polypropylene, polystyrene, polyurethane, nylon, polytetrafluoroethylene, etc.), microcrystalline or synthetic wax, metal oxides (e.g. aluminum, tin, titanium, etc.), silicates (e.g. aluminum, zirconium, etc.), chalk, chitin, clay, microcrystalline cellulose, perlite, sericite, silica, talc and so forth.

In a further particular embodiment, the scrubbing layer may comprise a fabric including fibers or yarns having a relatively coarse texture and/or having an average diameter greater than 75 microns and more desirably may have diameters in excess of about 100 microns. In a further aspect the filaments and/or yarns may have diameters between about 75 microns and about 1000 microns or in further aspects between about 100 microns and about 500 microns. Suitable polymers for forming the large fibers and/or yarns include, but are not limited to, polyolefins (e.g. polyethylene and polypropylene), polyesters (e.g. polyethylene terephthalate), polyamides (e.g. nylon), and combinations thereof. A specific example of material suitable for use in the scrubbing layer include a fabric woven from filament bundles or yarns ranging in size between about 200-800 microns wherein the (i) the first filament bundle comprises individual nylon filaments having an average fiber size of approximately 60 microns and (ii) the second filament bundle comprises individual polyethylene terephthalate filaments having an average fiber size of approximately 20 microns. In certain embodiments, larger and/or abrasive staple length fibers may be used in the formation of the web or, in the alternative, may be integrated into the outer surface of the web such as by needling and/or entangling.

In a further particular embodiment, the scrubbing layer may comprise, for instance, multifilamentary aggregate fibers formed by the partial coalescence of a plurality of polymer strands (i.e. the individual fibers produced by the process) during a meltblown process or other melt-spun fiber-forming process to form an integral, fiber-like, generally non-circular structure in which substantially parallel polymeric filaments are joined along their sides. Such multifilamentary aggregates may have an effective diameter much greater than the individual strands normally obtained in meltblown or spunbond processes, and a complex cross-sectional shape more suitable for providing abrasion than can be achieved with conventional circular fibers, and can contribute to effective cleaning and abrasion.

In certain embodiments, it may be desirable that the polymeric material forming the protuberances, and in particular the polymeric material forming the nodules and/or fibers, have a hardness of at least 65, and still more desirably at least about 70, and still more desirably at least about 80. In certain embodiments, the polymeric material forming the protuberances may have a hardness of between 65 and 100 and, in still further embodiments, may have a hardness between about 70 and about 90. As used herein, hardness of the polymeric material is determined in accordance with ASTM D2240 (Type D). In still other embodiments, the polymeric material forming the protuberances, including nodules and/or fibers, may desirably have a flexural modulus of about 500 MPa and still more desirably may have a flexural modulus of about 800 MPa or greater. Flexural modulus is determined in accordance with ASTM D790. In an alternative embodiment, the polymeric material may have both the flexural modulus and hardness properties described herein above.

The second outer layer 14 may comprise one or more of the materials described above in relation to the first outer layer 12 and/or the scrubbing layer 16. The second outer layer 14 may be made from any suitable synthetic or natural material so as to provide a layer that is compliant and easily manipulated and bent in use. Desirably the second outer layer is liquid permeable and is sufficiently abrasion resistant to substantially avoid linting and/or pilling during application against the body. Optionally, the first and second outer layers 12, 14 may be selected to comprise different materials having distinctly different degrees of coarseness and/or hand-feel in order to provide still further skin treatment options and/or tactile sensations for the user. In a further aspect, while not shown, the first and second outer layers may be integral to one another. Alternatively, and as shown in reference to FIGS. 1 and 2, the first and second outer layers 12, 14 may be joined together along the periphery 20 of the article by one or more means known in the art. By way of example, the first and second outer layers may be joined to one another through the use of adhesive, thermal bonding, mechanical crimping, needle stitching, and so forth. In addition, it is noted that other adjacent layers may be further joined to the first and/or second outer layer through the use of similar methods to achieve increased article integrity as desired.

The cleaning article may further include one or more core layers. By way of example and in reference to FIGS. 2-4, the cleaning article 10 may optionally include a core member 18 to add or enhance the functionality of the cleaning article 10. In one aspect and in reference to FIGS. 2 and 3, the core member 18 may be located entirely within the core 22 of the article 10. More specifically, in one embodiment the core member 18 may be located between the scrubbing layer 16 and second outer layer 14. The core member 18 can comprise one or more different materials depending on the desired properties of the cleaning article 10. In one aspect, the core member 18 may provide or enhance the ability of the cleaning article 10 to generate foam such as through the use of a resiliently-deformable porous material. In this regard, the compression and expansion of the porous material works in combination with existing and/or applied cleanser to generate numerous bubbles and create a rich foam or lather. Highly porous, low density materials that are resiliently-deformable are well suited to providing such a function; suitable materials include, but are not limited to, through-air bonded nonwoven fabrics, porous or open cell foams, compressed viscose or cellulose, and so forth. By way of non-limiting example, materials capable of provide such a benefit include those described in U.S. Pat. No. 4,068,036 to Stanistreet et al., EP0665315B1 to Pike et al., U.S. Pat. No. 5,985,434 to Qin et al., U.S. Pat. No. 7,358,282 to Krueger et al., and US2003/155679 to Reeves et al., and so forth.

In a further aspect, the core member 18 may be employed to improve the ease of handling or handleability of the cleaning article such as by providing additional stability or bending stiffness to the cleaning article such that the article does not readily bend or fold onto itself under its own weight or the weight of any applied water or cleansers. The bending stiffness or stability of the article or core member can be increased by the use or addition of one or more supporting layers such as a scrim reinforcing material or by increasing the density or the degree of cross-linking or interstitial bonding within the materials comprising the core member 18. In this regard, the aforementioned materials suitable for foam generation may also be provided with relatively higher degrees of bonding or cross-linking in order to obtain the desired degree of bending stiffness and resiliency. The size and location of the core member 18 will vary with the selected material and function. In many embodiments, it will be desirable for the core member to be centrally located within the article and to have a size that is smaller than that of the article itself such that the core member does not extend to the edge or form a part of any edge seal.

In yet a further aspect, the core member 18 may be utilized to provide a visual or tactile cue to the user that the article is sufficiently wetted for use. By way of example, the core member 18 may comprise one or more materials that significantly expand upon wetting such that the user can easily see or feel an increase in the volume of the article and thereby understand when the article if sufficiently wet and ready for use. In this regard, the core member 18 may comprise a sealed packet or pouch containing highly water-swellable materials such as, for example, “superabsorbent” materials. Superabsorbent materials are well known and widely used in absorbent personal care articles such as diapers and other incontinence garments; non-limiting examples of which include alkali metal salts of polyacrylic acids, polyacrylamides, polyvinyl alcohol, ethylene maleic anhydride copolymers, polyvinyl ethers, hydroxypropylcellulose, polyacrylates, modified starch such as hydrolyzed acrylonitrile grafted starch, and so forth. The swellable or superabsorbent materials may be in any form suitable for use in the article, including, particles, fibers, flakes, spheres, and the like. The swellable material may be sealed within or between one or more layers of liquid permeable materials such as, for example, sheets of cellulosic tissue or meltblown. By way of non-limiting example, suitable superabsorbent materials and methods of incorporating the same into materials and/or pouches are described in U.S. Pat. No. 4,646,510 McIntyre, U.S. Pat. No. 5,458,592 to Abuto et al., U.S. Pat. No. 6,162,961 to Tanner et al. Alternatively, the expandable or swellable material may comprise an absorbent, swellable foam.

In a further aspect, one or more layers of the article may include one or more cleaning or exfoliating agents to assist with the desired function of the article. In this regard, the scrubbing layer and/or a core member 18 may be impregnated with or have applied thereto a cleaning formulation. Skin cleaning formulations are well-known in the art and may include one or more of the following ingredients: cleansing and/or foaming (lathering) surfactants, detergents, builders, foam stabilizers, astringents, essential oils, plant extracts, humectants, moisturizing agents, buffering agents, chelating agents, anti-microbial agents, pigments, colorants, fragrances, and so forth. Foam generating surfactants, i.e. lathering surfactants, are widely known and used and are particularly well suited for use in cleansing formulations included in the cleaning article of the present invention. By way of example, suitable foam generating surfactants include, but are not limited to, glucosides (e.g. alkyl glucosides, alkyl polyglucosides, etc.), betaines (e.g. cetyl betaine, cetyl dimethyl betaine, cocamidopropyl betaine, lauryl dimethyl carboxymethyl betaine, etc.), alkyl and alkyl ether sulfates (e.g. sodium lauryl sulfate sodium, sodium laureth sulfate, cetyl sulfate, etc.), alkoxylated fatty acid esters, sultaines (e.g. cocamidopropyl hydroxysultaine, etc.), amine oxides (e.g. lauramine oxide, cocoamine oxide, etc.), alkoyl isethionates (e.g. sodium cocoyl isethionate, sodium lauroyl isethionate, etc.), and so forth. Further, non-limiting examples of suitable cleaning formulations are described in U.S. Pat. No. 6,806,213 to Brooks, US2003/207632 to Brooks, US2005/136531 to Sosalla et al, and so forth. Desirably, one or more of the interior layers, such as the scrubbing layer or a core layer, includes an effective amount of a lathering surfactant to enable the formation of a rich lather upon repeatedly pressing and releasing the wet article. As but one specific example, the cleaning formulation may include a combination of the following ingredients: decyl glucoside, glycerin, cocamidopropyl betaine, PEG-7 glyceryl cocoate, tocopheryl acetate, malic acid, and a cosmetically acceptable preservative.

The article, and cleaning formulation, may be provided in either a moist or dry form as desired. By way of non-limiting example, cleaning formulations may be applied to a core layer by dipping, spraying, printing (e.g. flexographic, rotogravure, offset, etc.), gravure coating, flexographic coating, slot coating, foam application, and so forth. Often it will be desirable to apply the cleaning formulation in aqueous form and thereafter remove excess water by hot air drying or other methods in order to achieve either a dry product or a moist product with higher percentages of functional ingredients. In alternative embodiments, it is noted that a cleansing formulation may be separately and/or additionally impregnated in or applied to one or more of the other layers including the first outer layer, second outer layer, or scrubbing layer. In certain embodiments, it will be desirable for the article to comprise, based upon its dry weight, between about 1% and 500% by weight of a cleaning formulation and/or a lathering surfactant. In still further embodiments, it will be desirable for the article to comprise between about 1% and about 250%, and still more desirably between about 5% and about 100%, of a cleaning formulation and/or lathering surfactant (based upon the dry weight of the article).

In a particular embodiment and in reference to FIG. 4, the cleaning article may include multiple core members so as to improve and/or provide multiple distinct functions of the same. By way of example, the cleaning article 10 may include a first core member 18 comprising a resiliently-deformable porous layer capable of improving foam generation and handleability. In addition, the cleaning article may further include a second core member 19 comprising a porous layer impregnated with a cleaning formulation. Thus, after wetting the article 10, a user's squeezing and releasing of the article 10 causes the cleaning formulation (not shown) to transfer to outer layers 12, 14 and for air to be draw into and pushed throughout the layers of the article 10 thereby aiding in the development of a rich foamy lather.

In a further aspect, any one or more layers in the cleaning article may optionally include one or more additives or topical agents in order to modify or improve its inherent hydrophilic and/or hydrophobic character. Often it will be desirable to increase the wettability or hydrophilic characters of a layer such as, for example, by the application or inclusion of wetting agents and/or surfactants. As a further option, one or more layers may include pigments, opacifying agents, softening agents, particulates, fragrances and so forth as desired to impart or improve one or more physical or aesthetic attributes. The materials comprising the various layers may also optionally be physically treated as desired to enhance or improve additional characteristics such as, for example, hand (feel), appearance, durability, and so forth. In this regard, examples of commonly employed treatments include, but are not limited to, embossing, stretching, creping, printing, needling and so forth.

In still a further aspect, the second side 13 of the article may include one or more elements designed to assist the user with the use, handling and/or manipulation of the cleaning article. By way of example, and in reference to 11, the flap 30 forms a strap extending across the article capable of being lifted upwardly away from the article and the user to insert their fingers thereunder. As a further example, the article 10 may include upwardly movable flaps 30 that form a pocket sized to allow a user to insert fingers therein. The flap(s) may comprise the same or different material than that comprising the second outer layer. In one aspect, the flap(s) may be integrally formed from the second outer layer. Alternatively, the flap(s) may be separately formed from and attached to the article such as, for example, be attached to the article along the peripheral edge seal.

The cleaning articles can, optionally, include one or more additional elements or components as are known and used in the art including, but not limited to, the use of fold lines, pad embossing, printing on one or more of the individual layers, individual article wrappers, and so forth. Still further additional features and various constructions are known in the art. Thus, while the invention has been described in detail with respect to specific embodiments and/or examples thereof, it will be apparent to those skilled in the art that various alterations, modifications and other changes may be made to the invention without departing from the spirit and scope of the same. It is therefore intended that the claims cover or encompass all such modifications, alterations and/or changes.

What is claimed is:

1. A method of cleaning the skin comprising:

(i) providing a skin cleaning article a. said article having a maximum diameter of between about 5 cm and about 15 cm and having at least first and second layers, b. said first layer having first and second opposed surfaces and further having a plurality of discrete apertures extending there through and individually having an area between 8 $mm^2$ and 700 $mm^2$, c. the first layer includes first and second regions, said first and second regions each comprising between 25% and 50% of the first layer and wherein a pattern of apertures is located in each of said first and second regions and further wherein the pattern of apertures within said first and second regions are distinct from one another, d. wherein the apertures in the first region comprise between 5-65% of the first region and the apertures of the second region comprise between 5-45% of the second region and further wherein apertures in the first region occupy at least 15% more area than the apertures of the second region, e. said second layer having first and second opposed surfaces wherein the first surface of the second layer has a rougher hand feel than the outer surface of the first layer, f. wherein the first surface of the second layer is adjacent the second surface of the first layer and further wherein said first surface of said second layer is exposed via the apertures in the first layer and in a recessed position relative to the first surface of the first layer;

(ii) applying water or cleansers to the article thereby forming a wetted article; and then (iii) pressing and rubbing the first side of the first layer against the skin wherein the recessed first surface of the second layer directly contacts the skin through the apertures and cleans the skin.

2. The method of claim 1 wherein the apertures within the first layer have a plurality of different sizes such that selected individual apertures in the first region are at least 20% larger by area than selected apertures in the second region.

3. The method of claim 2 wherein the apertures within the first region have (i) a minimum diameter of 4 mm and a maximum diameter of 20 mm and (ii) an area of between 12 $mm^2$ and 300 $mm^2$.

4. The method of claim 1 wherein the first layer comprises a fibrous material having an average fiber diameter of less than about 50 microns and further wherein the first surface of said second layer comprises a material having polymeric protuberances thereon, said protuberances having an average diameter between about 75 microns and about 1000 microns and a hardness of between 65 and 100 as measured according to ASTM D2240 (Type D).

5. The method of claim 4 wherein the protuberances comprise a polymeric material having a hardness between 65 and about 90 as measured according to ASTM D2240 (Type D) and further having a flexural modulus of at least 500 MPa.

6. The method of claim 1 wherein the first layer comprises a fibrous material having an average fiber diameter of less than about 50 microns and a basis weight between about 50-175 $g/M^2$ and further wherein the first surface of the second layer has yarns or fibers exposed thereon that have an average diameter of between about 75 microns and about 2000 microns.

7. The method of claim 1 wherein the average edge-to-edge distance between adjacent apertures is smaller in the first region relative to the second region.

8. The method of claim 1 wherein the first region has a greater number of apertures per unit area than the second region.

9. The method of claim 1 wherein the first and second regions are concentrically located relative to one another.

10. The method of claim 1 wherein the first and second regions are separated by a diameter line lacking any apertures and having a width of at least about 5 mm.

11. The method of claim 10 wherein the first and second regions each comprise about 50% of the first layer.

12. The method of claim 1 wherein said article further includes a third layer and wherein the first and third layers are joined at the periphery of the article and wherein the second layer is located between the first and third layers.

13. The method of claim 12 wherein said article further includes a fourth layer located between said second and third layers and wherein said fourth layer comprises a resiliently-deformable porous material.

14. The method of claim 1 wherein an inner portion of the article includes a skin cleaning composition comprising a lathering surfactant, a humectant and a moisturizing agent.

15. The method of claim 1 wherein the first layer comprises a compressible nonwoven web having a basis weight between about 50 to 175 g/$M^2$ and an average fiber diameter less than about 50 microns.

16. The method of claim 1 wherein the article has a curvilinear shape and a diameter between about 5 cm and about 10 cm.

17. A method of cleaning the skin comprising:

(i) providing a skin cleaning article a. said article having a maximum diameter of between about 5 cm and about 15 cm and having at least first and second layers, b. said first layer having first and second opposed surfaces and further having a plurality of discrete apertures extending there through and individually having an area between 8 $mm^2$ and 700 $mm^2$, c. the first layer includes first and second regions, said first and second regions each comprising between 25% and 50% of the first layer and wherein a pattern of apertures is located in each of said first and second regions and further wherein the pattern of apertures within said first and second regions are distinct from one another, d. wherein the apertures in the first region have a larger average size, by area, than that of the apertures in the second region, e. said second layer having first and second opposed surfaces wherein the first surface of the second layer has a rougher hand feel than the outer surface of the first layer, f. wherein the first surface of the second layer is adjacent the second surface of the first layer and further wherein said first surface of said second layer is exposed via the apertures in the first layer and in a recessed position relative to the first surface of the first layer;

(ii) applying water or cleansers to the article thereby forming a wetted article; and then (iii) pressing and rubbing the first side of the first layer against the skin wherein the recessed first surface of the second layer directly contacts the skin through the apertures and cleans the skin.

18. The method of claim 17 wherein the first layer comprises a compressible nonwoven web having a basis weight between about 50 to 175 g/$M^2$ and further comprises a fibrous material having an average fiber diameter of less than about 50 microns, and further wherein the first surface of said second layer comprises a material having polymeric protuberances thereon, said protuberances having an average diameter between about 75 microns and about 1000 microns and a hardness of between 65 and 100 as measured according to ASTM D2240 (Type D) and a flexural modulas greater than about 500 MPa.

19. The method of claim 17 wherein the first layer comprises a compressible nonwoven web having a basis weight between about 50 to 175 g/$M^2$ and further comprises a fibrous material having an average fiber diameter of less than about 50 microns, and further wherein the first surface of the second layer has yarns or fibers exposed thereon that have an average diameter of between about 75 microns and about 2000 microns.

20. The method of claim 17 wherein the apertures within the first region have (i) a minimum diameter of 4 mm and a maximum diameter of 20 mm and (ii) an area of between 12 $mm^2$ and 300 $mm^2$, and further wherein apertures in the first region are at least 20% larger by area than apertures in the second region and further wherein the the average edge-to-edge distance between adjacent apertures is smaller in the first region relative to the second region.

* * * * *